United States Patent
Frevert

(10) Patent No.: US 7,829,525 B2
(45) Date of Patent: Nov. 9, 2010

(54) FORMULATION FOR A PROTEIN PHARMACEUTICAL WITHOUT ADDED HUMAN SERUM ALBUMIN (HSA)

(75) Inventor: Jürgen Frevert, Berlin (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 777 days.

(21) Appl. No.: 10/565,111

(22) PCT Filed: Jul. 22, 2004

(86) PCT No.: PCT/DE2004/001635

§ 371 (c)(1),
(2), (4) Date: Feb. 19, 2007

(87) PCT Pub. No.: WO2005/007185

PCT Pub. Date: Jan. 27, 2005

(65) Prior Publication Data

US 2007/0134199 A1    Jun. 14, 2007

(30) Foreign Application Priority Data

Jul. 22, 2003   (DE) ............................... 103 33 317

(51) Int. Cl.
*A61K 38/00* (2006.01)
*C07K 14/00* (2006.01)

(52) U.S. Cl. .......................................... 514/2; 530/300
(58) Field of Classification Search ....................... None
See application file for complete search history.

(56) References Cited

U.S. PATENT DOCUMENTS

| 4,370,264 | A | * | 1/1983 | Kotitschke et al. | 530/383 |
| 4,895,716 | A | * | 1/1990 | Goldstein et al. | 424/85.5 |
| 5,512,547 | A | | 4/1996 | Johnson et al. | 514/21 |
| 6,136,294 | A | * | 10/2000 | Adjei et al. | 424/45 |
| 7,005,144 | B2 | * | 2/2006 | Hsu et al. | 424/549 |

FOREIGN PATENT DOCUMENTS

| JP | 07-502515 | 3/1995 |
| JP | 2000-508665 | 7/2000 |

OTHER PUBLICATIONS

Dootz, "Rote Liste 2003," *Rote Liste Service GmbH*, 2003.
Office Communication, issued in Chinese Patent Application No. 2006-520664, dated Jul. 27, 2010. (English translation).

* cited by examiner

*Primary Examiner*—Anand U Desai
(74) *Attorney, Agent, or Firm*—Fulbright & Jaworski L.L.P.

(57) ABSTRACT

A composition for stabilization of protein agents in pharmaceuticals, the composition comprising the following two constituents:
a) a surface active substance, in particular a non-ionic detergent (tenside), and
b) a mixture of at least two amino acids, wherein the at least two amino acids are either Glu and Gln or Asp and Asn.

22 Claims, No Drawings

FORMULATION FOR A PROTEIN PHARMACEUTICAL WITHOUT ADDED HUMAN SERUM ALBUMIN (HSA)

This application is a national phase application under 35 U.S.C. §371 of International Application No. PCT/DE2004/001635 filed 22 Jul. 2004, which claims priority to German Patent Application No. DE 103 33 317.7 filed 22 Jul. 2003. The entire text of each of the above-referenced disclosures is specifically incorporated herein by reference without disclaimer.

The present invention relates to a composition consisting of low molecular weight, non-peptidic substances, which stabilizes protein agents formulated in pharmaceuticals and which thereby forgoes the use of HSA. The present invention relates further to a pharmaceutical composition, which contains besides of the protein agent also the composition consisting of low molecular weight, non-peptidic substances.

The development of genetic engineering techniques provides a variety of novel pharmaceuticals whose agents represent proteins. In comparison to conventional pharmaceuticals, whose agents consist of low molecular weight substances, high molecular proteins display a high efficiency at low substance amounts and are thus applied in very low concentrations and dosages, respectively.

At such low concentrations and dosages, respectively, the manufacturers of pharmaceuticals face a problem. Namely, proteins have the property to adhere to solid surfaces. Because of this absorption a big portion of the applied protein agent can get lost. Of course, this effect is thereby the more serious the lower the concentration of the protein which is to be applied. Without an appropriate formulation the protein agent can even get totally lost.

A further problem of these pharmaceuticals and protein agents, respectively, resides in the high instability of proteins. For example, they can get easily oxidized (cysteine residues, methionine residues), and deaminated (asparagine), respectively, or they get cleaved in fragments and aggregate in higher order complexes, respectively. An efficient formulation should avoid such losses of protein agent and should guarantee a stable product.

Since the binding of proteins to surfaces is unspecific, the loss of agent can be prevented by adding a further (unspecific) protein in high excess. Since this additional protein should preferably have no pharmacological activity at all and should not stimulate the production of antibodies either, human serum albumin (HSA) is currently used for these purposes, which furthermore may be obtained at low prices, as it is applied in high amounts as plasma substitute. Thus currently several pharmaceuticals (various interferons, growth factors, coagulation factors, botulinum toxins and vaccines) are on the market, which contain HSA as stabilizer.

HSA is a product derived from human blood, which thus can be, despite of an obligatory examination, contaminated (such as by viruses) and which may provide a disease propagation to the recipient of the HSA containing pharmaceutical (especially as new pathogens (can) appear from time to time, which can not be registered by tests in time). Therefore, the authorities responsible for approval of pharmaceuticals urge to substitute HSA in newly approved pharmaceuticals. For this reason HSA should not be used in formulations of pharmaceuticals—provided that it can be substituted by other substances.

Human serum albumin (HSA) is due to various reasons particularly useful for the formulation of a protein agent. It is a protein and can therefore inhibit and neutralize, respectively, all unspecific reactions at the protein agent. This particularly applies for reactions at interfaces (liquid-solid, liquid-gas), which can lead to denaturing of the agent (Henson et al. (1970), Colloid Interface Sci 32, 162-165). The presence of HSA protects against denaturing. Besides, proteins have an affinity to surfaces to which they bind unspecifically by hydrophobic interactions (Norde W. (1995) Cells Mater 5, 97-112). The binding sites on surfaces can be saturated by an excess of HSA, so that the protein agent stays in solution, what is in particular obligatory, if the dose of the protein agent is to low.

Furthermore, the presence of HSA protects against denaturing processes during filling and optionally lyophilizing as well as during storage of the pharmaceutical (for example, against oxidative degradation processes or against a deamination of asparagine).

A protein protecting the agent in such a way should naturally not exhibit any pharmacological activity on its own, a prerequisite being fulfilled by HSA. HSA, being a human protein, should not serve as antigen, i.e. should not stimulate the antibody production. However, as HSA is isolated from blood and purified by physical chemical methods, it cannot be strictly excluded, that during the purification process neoepitopes, meaning new antigenic structures, arise, to which the recipient of the mixture of HSA and protein agent develops antibodies. This could lead to undesired side reactions. Due to possible side reactions the use of different proteins and a mixture of oligopeptides, respectively, is not desirable.

In principle gelatine can also be considered as stabilizer. It is an animal derived protein, which provokes immunological reactions and which could also be carrier of pathogenic agents.

The use of HSA and another suitable stabilizer for the protein agent, respectively, is also particularly important for pharmaceuticals, which contain protein agents, which are administered at very low dosages, as proteins are, in particular at low concentrations, extremely unstable and, moreover, bind at once to available unspecific binding sites. Consequently, they are lost for a therapeutical use. As examples for a protein agent, which is applied at very low dosages, the neurotoxins of *Clostridium botulinum* be mentioned. These highly active proteins are active at lowest amounts (they are, and the neurotoxin of *Clostridium botulinum* type A is, respectively, of all so far developed pharmaceuticals the one, which is administered in the lowest dosage (500 pg/vial). This very low quantity of protein gets lost unless a protecting agent is used.

It can be taken from the prior art, which essentially describes HSA as such a protecting agent, that there is a demand for providing alternatives to HSA as stabilizer of protein agents in pharmaceuticals. Accordingly, the inventors approached the problem, to develop a composition protecting/stabilizing protein agents in pharmaceuticals, which is at least as good as HSA.

The posed problem has been solved by the inventor by developing a composition consisting of low molecular weight, non-peptidic substances, which stabilizes protein agents formulated in pharmaceuticals and which composition thereby foregoes the use of HSA. This composition is termed composition for stabilization in the following.

According to a first aspect, the present invention relates to a composition free of unrelated protein, which composition can be formulated as pharmaceuticals with protein agents. This composition for stabilization is preferably based on low molecular weight substances, which have been produced according to the European Pharmacopoe (Ph. Eur.) and which are approved as pharmaceutical adjuvants. In particular, the composition allows foregoing HSA and guarantees not only a stable storage of the protein agents and the pharmaceutical without loss of agent, respectively, but also eliminates the risk, that the administered respective pharmaceutical is contaminated with infectious agents. It is surprising, that such low molecular weight and "simple" substances, as they are used according to the invention for the composition for stabilization, show the desired performance and can replace HSA.

The composition for stabilization according to the invention replaces HSA by a combination of different low molecular weight substances lacking side reactions, which substances protect against loss of protein agent by adsorption to surfaces as well as by denaturing and chemical degradation processes of the solved or lyophilized protein agents. Furthermore, the composition for stabilization prevents the degradation of the agent while storing it over a time period of >6 months at elevated temperature.

The composition for stabilization according to the invention exhibits the constituents denoted in claim 1, which constituents are:
 a) a surface active substance, in particular a non-ionic detergent (tenside), and
 b) a mixture of at least two amino acids, wherein the at least two amino acids are either Glu and Gln or Asp and Asn.

The composition for stabilization according to the invention contains according to another preferred embodiment one or more of the following further constituents:
 c) a disaccharide, preferably sucrose (cane sugar), trehalose or lactose,
 d) ethylenediaminetetraacetic acid (EDTA), preferably in form of one of its salts such as $Na_4$-EDTA.

Preferred compositions for stabilization according to the invention contain either the constituents a), b) and c), or the constituents a), b) and d), or the constituents a), b), c) and d). All these preferred compositions are either soluble in aqueous media or they are aqueous solutions.

It is advantageous, that all substances used in the composition for stabilization are approved of as adjuvants for pharmaceutical preparations and thus were toxicologically examinated in detail, which means that they can be admixed to the composition for stabilization according to the invention without further examinations. It was surprising, that an exactly defined compilation of these simple substances showed the desired performance, namely, to provide a stable serum albumin-free formulation for protein agents.

According to a second aspect, the present invention relates to a pharmaceutical composition containing a protein agent and the above-mentioned composition for stabilization, comprising the constituents a) and b), or one of the above-mentioned preferred compositions for stabilization.

The agent and the protein agent, respectively, is prepared preferably in an aqueous solution (dissolved), which contains the constituents a) and b) and optionally also c) and/or d). This solution can be lyophilized subsequently. If the solution is in fact to be lyophilized, the prior addition of constituent c) is particularly advantageous. After lyophilizing the pharmaceutical composition is present as powder, which can be reconstituted (preferably with water for injection purposes (WFI)).

Accordingly, the pharmaceutical composition is preferably present in form of a freeze-dried or vacuum-dried powder soluble in aqueous media. Prior to the therapeutical application the lyophilized composition and the powder, respectively, is preferably reconstituted with water for injection purposes (WFI). The pharmaceutical composition can never the less also be present in liquid form, preferably as aqueous solution.

Preferred pharmaceutical compositions of the present invention contain next to the above-mentioned constituents a) and b) as protein a coagulation factor like factor VIII (the antihemophylic globulin), a cytokine such as a interferon, in particularly such as inferone alpha, beta or gamma, an enzyme such as an urokinase or a streptokinase, an plasminogen activator or ultra pure neurotoxin (for a definition of "ultra pure neurotoxin" see further below) and a neurotoxin complex, respectively, from *Clostridium botulinum*, especially from *Clostridium botulinum* types A, B, C, D, E, F or G. As the clostridial toxins are formulated in lowest amounts as pharmaceutical, in particular their ultra pure form, they are the preferred protein. In particular preferred are ultra pure neurotoxins of the A and B type.

Further preferred pharmaceutical compositions of the present invention contain, besides the above-mentioned constituents a) and b) and the agent, additionally the above defined constituent c), the above-defined constituent d), or these two constituents together.

In both compositions according to the invention are the at least two amino acids (i) aspartic acid and asparagine, or (ii) glutamic acid and glutamine. However, preferably the compositions contain at least three (aspartic acid, asparagine, glutamic acid; aspartic acid, asparagine, glutamine; aspartic acid, glutamic acid, glutamine; asparagine, glutamic acid, glutamine) of these four amino acids, or even all four (aspartic acid, asparagine, glutamic acid and glutamine). Preferably the individual amino acids are used in concentrations of 20 to 200 mM, preferably 20 to 100 mM, in particular 50 mM. This corresponds in the case of a filling of 0.5 ml starting solution to the amount of from 1.3 mg to 14.7 and 1.3 to 7.4 mg, respectively, preferably about 3.7 mg per amino acid in the powder after drying.

In another preferred embodiment of both compositions of the present invention the surface active substance (the tenside) is a non-ionic detergent, preferably a polysorbate (like polysorbate 20 or polysorbate 80) or poloxamer (like poloxamer 184 or poloxamer 188). If the pharmaceutical composition is present in liquid form, the portion of polysorbate is preferably 0.01 to 0.5 wt.-%, preferably a portion of 0.2 wt.-%. This corresponds to the amount of 0.05 to 2.5 mg, preferably 1 mg polysorbate, after for example a freeze-drying process of 0.5 ml starting solution.

In a further preferred embodiment of both compositions of the present invention the disaccharide is sucrose, trehalose or lactose. Sucrose is especially preferred. Is the pharmaceutical composition according to the invention provided as solution, the solution contains preferably 2 to 10 wt.-%, more preferred 5 wt.-% of the disaccharide, in particular of the sucrose.

Further preferred is, as already described, the use of a constituent d), a complex former (chelator) exhibiting an additional stabilizing effect. The concentration of ethylenediaminetetraacetic acid in the starting solution of the pharmaceutical composition is preferably 0.1 to 1.0 mM, in particular 5 mM.

Both types of compositions according to the present invention exhibit preferably a pH-value of 5.0 to 8.5, more preferred a pH-value of 6.0 to 8.0, in particular of 6.0 to 7.0 and 6.5, respectively. The pH-value is optionally, if necessary and desired, respectively, adjusted with NaOH.

The initially already mentioned neurotoxins of *Clostridium botulinum*, in particular the *Clostridium botulinum* neurotoxins of type A and B, have to be formulated for pharmaceutical purposes in very low dosages. Thus, the quality of the composition for stabilization according to the invention can be verified particularly well by means of this agent, which is extremely complicated to handle. Other protein agents are formulated in considerably higher amounts; HSA can therefore be easier replaced by the compositions for stabilization according to the invention.

Type A *Clostridium botulinum* toxin (trade name Botox™, Allergan; Dysport™, Ipsen) has been applied for many years for therapy of different forms of dystonias (e.g. blepharospasms, torticollis), of spasticities, for treatment of hyperhydrosis, but also as well in the cosmetic area for removal of face wrinkles. This agent is a protein complex, which is synthesized by anaerobically growing bacteria (*Clostridium botulinum*). The active agent in this protein complex is a protein with a molecular weight of 150 kD, the botulinum neurotoxin (BoNT). This toxin and neurotoxin, respectively, acts at the motor end plate and inhibits the transduction of the nerve impulse to the muscle and leads therefore to a paralysis of this muscle. This mechanism of action allows applying the neurotoxin in diseases, in which the stimulus transduction is pathologically changed, i.e. an enhanced acetylcholine release occurs.

The botulinus toxins and neurotoxins, respectively, currently on the market are all based on the toxin complex from *Clostridium botulinum*, i.e. the neurotoxin. Essentially, the active molecule is embedded in an ensemble of proteins with different molecular weights: these are various hemagglutinins (15 kD, 19 kD, 35 kD, 52 kD) as well as a non-toxic non-hemagglutinic protein (NTNH, 120 kD). Without these so called protection proteins the isolated neurotoxin is very instable and is easily degraded by proteases. The protection proteins and the complexing proteins, respectively, are therefore for the real function of the nerve cell dispensable, but play a role in the stabilization of the susceptible neurotoxin. On the other hand there are hints, that these complexing proteins can exert an immunostimulatory function, which could be responsible for the production of antibodies in 5-10% of the patients, which leads inevitably to the end of the therapy with this type of neurotoxin ("secondary nonresponder"). Further it has to taken into account, that patients are strained with foreign protein (the complexing proteins), which is pharmacologically not absolutely necessary. Therefore it makes sense to apply the pure, complex protein-free neurotoxin as agent, but it needs, because of its low dose and lability, a particular efficient formulation.

Therefore, the prerequisite for the use of the complex protein-free neurotoxin (the complex protein-free neurotoxin is occasionally also termed an ultra pure neurotoxin) as agent in a pharmaceutical was to develop a pharmaceutical composition, which guarantees the stability of the biological function of the ultra pure neurotoxin over a longer period of time. This prerequisite has been met by the inventor by the provision of the composition for stabilization according to the invention.

The two pharmaceuticals on the basis of the neurotoxin of type A currently on the market contain as essential stabilizer HSA (Botox™ contains for 100 units agent 0.5 mg HSA and additionally 0.9 mg sodium chloride, while Dysport™ contains for 500 units agent 0.125 mg HSA and furthermore 2.5 mg lactose). Neurobloc™, based on the toxin complex type B, consists in the case of 2000 units of a solution with 500 µg/ml HSA, 0.01 M sodium succinate and 0.1 M sodium chloride. As described above, the HSA serves in particular the purpose to prevent the adsorption of the toxin to the vial walls (glass vials, syringes, cannulae) and to protect against denaturing. Without the serum albumin (or without substances which substitute this effect), the toxin inevitably gets lost. This is mainly due to the fact, that the amount of neurotoxin in these pharmaceuticals is very low (Botox™ contains 5 ng, Dysport™ 20 ng toxin complex per packaging unit ("vial")). Provided, that no other protein is present, the sufficiently present unspecific protein binding sites are occupied by the toxin. In the presence of a high excess (>50,000 fold), as in the mentioned pharmaceuticals, the binding sites are occupied by HSA, so that the neurotoxin complex stays in solution. The probability that the ultra pure complex-free neurotoxin adsorbs to the solid surface of the container is considerably higher, because the protein amount of pure neurotoxin for a dose of 100 units is only 500 pg.

Patent application WO 01/58472 describes a formulation for a complex from *Clostridium botulinum* of type A, which consists essentially of hydroxyethyl starch. Examples are given in which the formulation is stable for one year. With the ultra pure, thus complex protein-free, neurotoxin no examinations are described. However, it is stated, that "the toxin protein has a marked instability upon removal of the hemagglutinin protein". Furthermore in the case of the ultra pure botulinum toxin it is noted, that the "pure botulinum toxin is a so labile but it has limited practical utility to prepare a pharmaceutical composition." However, it is not mentioned, that the described formulation on basis of the hydroxyethyl starch is also efficient for stabilizing the ultra pure neurotoxin.

A HSA containing formulation of ultra pure neurotoxin is described in U.S. Pat. Nos. 5,512,547 and 5,756,468. In the first patent a formulation is described containing HSA as well as trehalose and maltotriose or related sucrose. The second patent specifies a formulation, which contains in addition to these saccharides methionine or cysteine. The necessity to use HSA in a formulation for the ultra pure neurotoxin is demonstrated in a publication as well (Goodenough et al. (1992) Appl Environm Microbiol 58 3426-3428).

The pharmaceutical composition according to the invention can be produced for example as follows: A solution of the agent (e.g. of a neurotoxin from *Clostridium botulinum*) is diluted with the composition for stabilization (in form of an aqueous solution) to a concentration of 1.0-1.2 ng/ml (≅200 units/ml) and is subsequently sterile filtered. 0.5 ml of this dilution are filled in vials, lyophilized or vacuum-dried and stored until the therapeutical application. One vial contains therefore a lyophilized composition or a vacuum-dried powder with about 100 units of the neurotoxin. For administration to the patient the lyophilized composition or the powder is reconstituted with 2-8 ml WFI, depending on the indication. The described composition for stabilization according to the present invention guarantees a complete recovery of the protein agent (the neurotoxin) after dilution, sterile filtering, filling and lyophilizing. The lyophilized composition is at 37° C. stable for more than 6 months.

EXAMPLE 1

It was to be checked, if the use of the composition for stabilization according to the invention provides for a higher recovery in comparison to a phosphate buffer and a composition of a phosphate buffer and polysorbate, respectively.

All used excipients have been obtained from the manufacturers at pharmaceutical quality. *Clostridium botulinum* neurotoxin type A can be obtained from List Biological Laboratories, Inc. Campell, Calif., U.S.A. and was produced, respectively, according DasGupta, B. R. (1984) Toxicon 3, 415-424.

A solution of *Clostridium botulinum* neurotoxin type A (168 µg/ml) was diluted with a composition for stabilization according to the present invention to a concentration of 0.5 µg/ml. The composition for stabilization was 50 mM with regard to aspartic acid, asparagine, glutamic acid and glutamine, contained 0.05 weight-% polysorbate 20 and exhibited a pH of 7.5.

A further dilution to 1.2 ng/ml ($\cong$200 LD$_{50}$/ml) was carried out with various solutions (see table 1). After filtration over a 0.22μ filter, 0.5 ml of these further diluted solutions were filled in a glass vial (6 R, Münnerstädt) and stored at 37° C. The vials were sealed with rubber stoppers. After storing for 15 h, the concentration of the neurotoxin in the individual solutions was determined by a conventional specific enzyme immunoassay (EIA).

TABLE 1

| Composition | Concentration and content, respectively | Recovery (%) |
|---|---|---|
| 1. Solution | | |
| Sodium phosphate | 50 mM | 0 |
| 2. Solution | | |
| Sodium phosphate | 50 mM | 62.5 |
| Polysorbate 20 | 0.05 wt.-% | |
| 3. Solution | | |
| Aspartic acid | 50 mM | 111 |
| Asparagine | 50 mM | |
| Glutamic acid | 50 mM | |
| Glutamine | 50 mM | |
| Polysorbate 20 | 0.05 wt.-% | |
| EDTA | 0.5 mM | |

The selected formulation resulted in a complete recovery after incubation at 37° C.

EXAMPLE 2

It was to be examined, if a pharmaceutical composition according to the invention with 200 units neurotoxin type A/ml (1.2 ng/ml) is stable over a long period of time.

From a stock solution with 0.5 μg/ml *Clostridium botulinum* neurotoxin type A a dilution with a concentration of 1.2 ng/ml was produced by using the in table 2 listed compositions according to example 1. After sterile filtering, 0.5 ml of these compositions were filled in vials, which were then sealed with rubber stoppers. After storing for 15 h at 4° C. and 37° C. the amount of neurotoxin type A was determined in an ELISA.

After 8 months of storing at 4° C. the biological activity in the vials was determined by means of an ex vivo-assay. Therefore, the activity of the compositions was determined by the mouse diaphragm assay (Wohlfahrt K. et al. (1997) Naunyn-Schmiedebergs Arch. Pharmcol. 355, 225-340)

TABLE 2

| Composition | Concentration and content, respectively | 15 h 4° C. | 15 h 37° C. | Recovery (%) after 8 months (4° C.) |
|---|---|---|---|---|
| Aspartic acid | 50 mM | 100 | 21 | 100 |
| Asparagine | 50 mM | | | |
| Glutamic acid | 50 mM | | | |
| Glutamine | 50 mM | | | |
| Polysorbate 80 | 0.05 wt.-% | | | |
| Aspartic acid | 50 mM | 12 | 0 | — |
| Asparagine | 50 mM | | | |
| Glutamic acid | 50 mM | | | |
| Glutamine | 50 mM | | | |

A solution consisting of the amino acids Asn, Asp, Gln and Glu (each 50 mM) and polysorbate 80 was stable at 4° C. for at least 8 months.

EXAMPLE 3

It was to be examined, which stabilizing effect different mixtures of amino acids exhibit. The pharmaceutical compositions were again adjusted to a concentration of 1.2 ng *Clostridium botulinum* neurotoxin type A/ml (200 units/ml) (dilutions were carried out according to example 1 and with the in table 3 listed solutions, respectively) and were stored at 4° C. after sterile filtering over a 0.22μ filter. The results of a neurotoxin determination in the enzyme immuno assay are displayed in table 3.

TABLE 3

| Composition | Concentration and content, respectively | pH-value | Recovery (%) |
|---|---|---|---|
| Aspartic acid | 50 mM | 7.5 | 65 |
| Asparagine | 50 mM | | |
| EDTA | 0.5 mM | | |
| Polysorbate 20 | 0.05 wt.-% | | |
| Sucrose | 1 wt.-% | | |
| Glutamic acid | 50 mM | 7.5 | 12 |
| Glutamine | 50 mM | | |
| EDTA | 0.5 mM | | |
| Polysorbate 20 | 0.05 wt.-% | | |
| Sucrose | 1 wt.-% | | |
| Glutamic acid | 50 mM | 7.5 | 10 |
| EDTA | 0.5 mM | | |
| Polysorbate 20 | 0.05 wt.-% | | |
| Sucrose | 1 wt.-% | | |
| Aspartic acid | 50 mM | 7.5 | 106 |
| Asparagine | 50 mM | | |
| Glutamic acid | 50 mM | | |
| Glutamine | 50 mM | | |
| EDTA | 0.5 mM | | |
| Polysorbate 20 | 0.05 wt.-% | | |
| Sucrose | 1 wt.-% | | |

A mixture of all four amino acids resulted in a complete recovery of the agent.

EXAMPLE 4

It was to be examined at which pH-value the developed formulations provided the highest recovery. The formulation was prepared at pH-values of 6.0 to 8.0 at a concentration of 1.2 mg/ml *Clostridium botulinum* neurotoxin type A and was stored at 37° C. after filtration over a 0.22μ filter. The results of a neurotoxin determination in the enzyme immunoassay are displayed in table 4.

TABLE 4

| Composition | Concentration and content, respectively | pH-value | Recovery after 2 Days | Recovery after 9 Days | Recovery after 21 Days |
|---|---|---|---|---|---|
| Aspartic acid | 50 mM | 6.0 | 100 | 95 | 78 |
| Asparagine | 50 mM | | | | |
| Glutamic acid | 50 mM | | | | |
| Glutamine | 50 mM | | | | |
| EDTA | 0.5 mM | | | | |
| Polysorbate 20 | 0.05 wt.-% | | | | |
| Sucrose | 1 wt.-% | | | | |
| Aspartic acid | 50 mM | 6.5 | 100 | 92 | 83 |
| Asparagine | 50 mM | | | | |
| Glutamic acid | 50 mM | | | | |

TABLE 4-continued

| Composition | Concentration and content, respectively | pH-value | Recovery after 2 Days | 9 Days | 21 Days |
|---|---|---|---|---|---|
| Glutamine | 50 mM | | | | |
| EDTA | 0.5 mM | | | | |
| Polysorbate 20 | 0.05 wt.-% | | | | |
| Sucrose | 1 wt.-% | | | | |
| Aspartic acid | 50 mM | 7.0 | 100 | 85 | 75 |
| Asparagine | 50 mM | | | | |
| Glutamic acid | 50 mM | | | | |
| Glutamine | 50 mM | | | | |
| EDTA | 0.5 mM | | | | |
| Polysorbate 20 | 0.05 wt.-% | | | | |
| Sucrose | 1 wt.-% | | | | |
| Aspartic acid | 50 mM | 7.5 | 100 | 61 | 55 |
| Asparagine | 50 mM | | | | |
| Glutamic acid | 50 mM | | | | |
| Glutamine | 50 mM | | | | |
| EDTA | 0.5 mM | | | | |
| Polysorbate 20 | 0.05 wt.-% | | | | |
| Sucrose | 1 wt.-% | | | | |
| Aspartic acid | 50 mM | 8.0 | 85 | 17 | 6 |
| Asparagine | 50 mM | | | | |
| Glutamine acid | 50 mM | | | | |
| Glutamine | 50 mM | | | | |
| EDTA | 0.5 mM | | | | |
| Polysorbate 20 | 0.05 wt.-% | | | | |
| Sucrose | 1 wt.-% | | | | |

The best recoveries were achieved at pH-values of 6.9 and 6.5.

EXAMPLE 5

It was to be examined, at which concentration of the four amino acids aspartic acid, asparagines, glutamic acid and glutamine the highest recovery is achieved. Starting from a dilution of *Clostridium botulinum* neurotoxin type A with 0.5 µg/ml, a further dilution to 1.2 µg/ml was produced and filled in 6R-vials at a dosage of 0.5 ml per vial after filtration over a 0.22µ filter. After sealing with a rubber stopper they were stored at 4° C. for 15 h and subsequently the amount of neurotoxin/vial was determined.

TABLE 5 a

| Composition | Concentration and content, respectively | pH-value | Recovery (in %) |
|---|---|---|---|
| Aspartic acid | 200 mM | 7.5 | 19 |
| Asparagine | 200 mM | | |
| Glutamic acid | 200 mM | | |
| Glutamine | 200 mM | | |
| Polysorbate 20 | 0.01 wt.-% | | |
| EDTA | 0.5 mM | | |
| Sucrose | 5 wt.-% | | |
| Aspartic acid | 100 mM | 7.5 | 56 |
| Asparagine | 100 mM | | |
| Glutamic acid | 100 mM | | |
| Glutamine | 100 mM | | |
| Polysorbate 20 | 0.01 wt.-% | | |
| EDTA | 0.5 mM | | |
| Sucrose | 5 wt.-% | | |
| Aspartic acid | 50 mM | 7.5 | 93 |
| Asparagine | 50 mM | | |
| Glutamic acid | 50 mM | | |
| Glutamine | 50 mM | | |
| Polysorbate 20 | 0.01 wt.-% | | |
| EDTA | 0.5 mM | | |
| Sucrose | 5 wt.-% | | |

TABLE 5 b

| Composition | Concentration and content, respectively | pH-value | Recovery (%) |
|---|---|---|---|
| Aspartic acid | 50 mM | 6.5 | 79 |
| Asparagine | 50 mM | | |
| Glutamic acid | 50 mM | | |
| Glutamine | 50 mM | | |
| EDTA | 0.5 mM | | |
| Polysorbate 20 | 0.2 wt.-% | | |
| Sucrose | 5 wt.-% | | |
| Aspartic acid | 50 mM | 6.5 | 86 |
| Asparagine | 50 mM | | |
| Glutamic acid | 50 mM | | |
| Glutamine | 50 mM | | |
| EDTA | 0.5 mM | | |
| Polysorbate 20 | 0.2 wt.-% | | |
| Sucrose | 5 wt.-% | | |
| Aspartic acid | 20 mM | 6.5 | 0 |
| Asparagine | 20 mM | | |
| Glutamic acid | 20 mM | | |
| Glutamine | 20 mM | | |
| EDTA | 0.5 mM | | |
| Polysorbate 20 | 0.2 wt.-% | | |
| Sucrose | 5 wt.-% | | |
| Aspartic acid | 10 mM | 6.5 | 0 |
| Asparagine | 10 mM | | |
| Glutamic acid | 10 mM | | |
| Glutamine | 10 mM | | |
| EDTA | 0.5 mM | | |
| Polysorbate 20 | 0.2 wt.-% | | |
| Sucrose | 5 wt.-% | | |

In case of the liquid formulation a concentration of the amino acids of 50 mM proofed to be efficient for the recovery of the agent.

EXAMPLE 6

It was examined, which composition of amino acids resulted in the highest recovery after freeze-drying, wherein in this approach no EDTA was used. The filled solution (0.5 ml) was freeze-dried and stored over night at 4° C. The lyophilized compositions were reconstituted in 0.5 ml water for injection purposes. The neurotoxin concentration was determined by enzyme immunoassay.

TABLE 6

| Composition | Concentration and content, respectively | pH-value | Recovery (%) in lyophilized compositions |
|---|---|---|---|
| Aspartic acid | 100 mM | 6.5 | 0 |
| Asparagine | 100 mM | | |
| Sucrose | 5 wt.-% | | |
| Polysorbate 80 | 0.2 wt.-% | | |
| Aspartic acid | 50 mM | 6.5 | 20 |
| Asparagine | 50 mM | | |
| Sucrose | 5 wt.-% | | |
| Polysorbate 80 | 0.2 wt.-% | | |
| Aspartic acid | 100 mM | 6.5 | 9.3 |
| Glutamic acid | 100 mM | | |
| Asparagine | 100 mM | | |
| Sucrose | 5 wt.-% | | |
| Polysorbate 80 | 0.2 wt.-% | | |
| Aspartic acid | 50 mM | 6.5 | 56 |
| Glutamic acid | 50 mM | | |
| Asparagine | 50 mM | | |
| Sucrose | 5 wt.-% | | |
| Polysorbate 80 | 0.2 wt.-% | | |
| Aspartic acid | 100 mM | 6.5 | 20 |
| Glutamic acid | 100 mM | | |
| Sucrose | 5 wt.-% | | |

TABLE 6-continued

| Composition | Concentration and content, respectively | pH-value | Recovery (%) in lyophilized compositions |
|---|---|---|---|
| Polysorbate 80 | 0.2 wt.-% | | |
| Aspartic acid | 50 mM | 6.5 | 87 |
| Asparagine | 50 mM | | |
| Glutamic acid | 50 mM | | |
| Glutamine | 50 mM | | |
| Sucrose | 5 wt.-% | | |
| Polysorbate 80 | 0.2 wt.-% | | |

The highest recovery of the agent in lyophilized compositions was achieved, when all four amino acids were present in the composition and in a concentration of 50 mM.

EXAMPLE 7

Starting from a predilution of a *Clostridium botulinum* neurotoxin type A in a solution (which was 50 mM each for aspartic acid, asparagine, glutamic acid and glutamine, and 0.5 mM for EDTA, and which solution contained furthermore 0.2 wt.-% polysorbate 80 and 5 wt.-% sucrose and which exhibited a pH of 6.5), a final dilution of 1.26 ng neurotoxin type A/ml (200 U/ml) in a solution of identical composition was produced and filtered over a 0.22µ membrane filter. 0.5 ml thereof were pipetted in 6 R glass vials and subsequently lyophilized. The lyophilized compositions were dissolved in WFI. The agent content (neurotoxin type A) was determined in the enzyme immunoassay. 96 wt.-% of the agent were detected. For verification of the biological activity of the recovered agent the lyophilized compositions were dissolved and tested on the diaphragm. The lyophilized composition of one vial contained 110 units (corresponding to 110% recovery).

EXAMPLE 8

In analogy to example 7, lyophilized compositions were produced and subsequently stored at 37° C. After three months the agent content was determined in the immunoassay. 94 wt.-% of the input agent were detected. The verification of the activity/vial in the biological assay (diaphragm assay) resulted in a content of 102 units/vial.

EXAMPLE 9

Starting from a predilution of interferon beta in a solution (which was for one approach without, for the other one with 0.5 mM EDTA), which was 50 mM each for aspartic acid, asparagine, glutamic acid and glutamine, and which solution contained furthermore 0.2 wt.-% polysorbate 80 and 5 wt.-% sucrose and which exhibited a pH of 7.0, final dilutions with 20 µg/ml (4 Mio international units/ml) in solutions with corresponding composition were produced and filtered over a 0.22µ membrane filter. 1 ml of each filtrate was pipetted in 6 R glass vials and subsequently lyophilized. The lyophilized compositions were solved in WFI. The agent content (interferon beta) was determined in the enzyme immunoassay. 18.8 (without EDTA) and 19.6 µg (0.5 mM EDTA), respectively, of the agent were detected. For verification of the biological activity of the recovered agent the lyophilized compositions were dissolved and the activity was determined in the conventional bio assay (inhibition of the cytopathic effect on VERO-cells in comparison to the reference standard). 94 and 95%, respectively, of the input biological activity were recovered.

EXAMPLE 10

Starting from a predilution of blood coagulation factor VIII in a solution (which was 50 mM each for aspartic acid, asparagines, glutamic acid and glutamine and 0.5 mM for EDTA, and which furthermore contained 0.2 wt.-% polysorbate and 5 wt.-% sucrose and which exhibited a pH of 7.3), a final dilution with 250 international units/ml in a solution of identical composition was produced and filtered over a 0.22µ membrane filter. In one approach polysorbate 20 was used, in the other polysorbate 80. 1 ml of each of the obtained filtrates was pipetted in 6 R-glass vials and subsequently lyophilized. The lyophilized compositions were dissolved in WFI. The agent content (blood coagulation factor VIII) was determined in the conventional coagulation test. 238 (P 20) and 245 (P 80) international units per vial, respectively, were detected.

EXAMPLE 11

Starting from a predilution of streptokinase in solution (which was 50 mM each for aspartic acid, asparagines, glutamic acid and glutamine and 0.5 mM for EDTA and which contained furthermore 0.2 wt.-% polysorbate 80 and 2.5, 5 and 7.5 wt.-% sucrose, respectively, and which exhibited a pH of 7.0), a final dilution of 250,000 international units/ml in solutions of corresponding composition was produced and filtered over a 0.22µ membrane filter. 1 ml of each filtrate was pipetted into 6 R glass vials and subsequently lyophilized. The lyophilized compositions were dissolved in WFI. The agent content (streptokinase) was determined in the standard fibrinolysis assay. 236,500, 247,000 and 242,500 international units per vial, respectively, were detected.

The invention claimed is:

1. A composition free of human serum albumin for stabilization of protein agents in pharmaceuticals, the composition comprising the following constituents:
   a) a surface active substance, and
   b) a mixture of at least two amino acids, wherein the at least two amino acids are either Glu and Gln or Asp and Asn.

2. The composition according to claim 1, further comprising at least one of the following constituents selected from the group consisting of a sucrose, trehalose, lactose, ethylenediaminetetraacetic acid (EDTA), and a salt of EDTA.

3. The composition according to claim 2, comprising any-one of the following constituent groups:
   a) a surface active substance, a mixture of at least two amino acids, wherein the at least two amino acids are either Glu and Gln or Asp and Asn, and at least one of sucrose, trehalose, or lactose,
   b) a surface active substance, a mixture of at least two amino acids, wherein the at least two amino acids are either Glu and Gln or Asp and Asn, and EDTA or a salt of EDTA
   c) a surface active substance, a mixture of at least two amino acids, wherein the at least two amino acids are either Glu and Gln or Asp and Asn, and at least one of sucrose, trehalose, lactose, EDTA, or a salt of EDTA.

4. The composition according to claim 1, wherein the composition is either soluble in aqueous media or is present as aqueous solution.

5. A pharmaceutical composition comprising a protein agent and a composition free of human serum albumin for stabilization of protein agents in pharmaceuticals, the composition comprising the following constituents:
   a) a surface active substance, and
   b) a mixture of at least two amino acids, wherein the at least two amino acids are either Glu and Gln or Asp and Asn.

6. The pharmaceutical composition according to claim 5, wherein the pharmaceutical composition is present as a freeze-dried or vacuum-dried powder, which is soluble in aqueous media.

7. The pharmaceutical composition according to claim 5, wherein the protein agent is a coagulation factor, a cytokine, an enzyme, a plasminogen activator, an ultra pure neurotoxin or a neurotoxin complex.

8. The composition for stabilization according to claim 1, wherein the at least two amino acids are (i) aspartic acid, asparagine, glutamic acid; (ii) aspartic acid, asparagine, glutamine; (iii) aspartic acid, glutamic acid, glutamine; (iv) asparagine, glutamic acid, glutamine; or (v) aspartic acid, asparagine, glutamic acid and glutamine.

9. The pharmaceutical composition according to claim 8, wherein the concentrations of the individual amino acids are in each case 20 to 200 mM.

10. The pharmaceutical composition according to claim 8, wherein the surface active substance is a non-ionic detergent.

11. The pharmaceutical composition according to claim 10, wherein the non-ionic detergent is a polysorbate or a poloxamer.

12. The pharmaceutical composition according to claim 8, wherein the disaccharide is sucrose, trehalose or lactose.

13. The pharmaceutical composition according to claim 8, wherein the pH value of the composition in solution is 5.0 to 8.5.

14. The pharmaceutical composition of claim 5, wherein the at least two amino acids are (i) aspartic acid, asparagine, glutamic acid; (ii) aspartic acid, asparagine, glutamine; (iii) aspartic acid, glutamic acid, glutamine; (iv) asparagine, glutamic acid, glutamine; or (v) aspartic acid, asparagine, glutamic acid and glutamine.

15. The pharmaceutical composition according to claim 13, wherein the pH value of the composition in solution is 6.0 to 8.0.

16. The pharmaceutical composition according to claim 13, wherein the pH value of the composition in solution is 6.0 to 7.0.

17. The pharmaceutical composition according to claim 13, wherein the pH value of the composition in solution is 6.5.

18. The pharmaceutical composition according to claim 11, wherein the polysorbate or poloxamer is polysorbate 20, polysorbate 80, poloxamer 184, or poloxamer 188.

19. The composition of claim 1, wherein the surface active agent is a non-ionic detergent.

20. The composition of claim 19, wherein the non-ionic detergent is tenside.

21. The composition of claim 5, wherein the surface active agent is a non-ionic detergent.

22. The composition of claim 21, wherein the non-ionic detergent is tenside.

* * * * *